(12) United States Patent
Wu

(10) Patent No.: US 10,433,940 B2
(45) Date of Patent: Oct. 8, 2019

(54) ELECTRIC TOOTHBRUSH

(71) Applicant: Xiaowang Wu, Zhejiang (CN)

(72) Inventor: Xiaowang Wu, Zhejiang (CN)

( * ) Notice: Subject to any disclaimer, the term of this patent is extended or adjusted under 35 U.S.C. 154(b) by 200 days.

(21) Appl. No.: 15/437,459

(22) Filed: Feb. 21, 2017

(65) Prior Publication Data

US 2018/0064516 A1 Mar. 8, 2018

(30) Foreign Application Priority Data

Sep. 8, 2016 (CN) .......................... 2016 1 0810362

(51) Int. Cl.
| | |
|---|---|
| A61C 17/34 | (2006.01) |
| A45B 9/04 | (2006.01) |
| A61C 17/22 | (2006.01) |
| A46B 9/04 | (2006.01) |
| B22D 25/02 | (2006.01) |
| C22C 21/06 | (2006.01) |

(52) U.S. Cl.
CPC ............ *A61C 17/3481* (2013.01); *A46B 9/04* (2013.01); *A61C 17/22* (2013.01); *A61C 17/221* (2013.01); *A61C 17/224* (2013.01); *A61C 17/225* (2013.01); *A61C 17/34* (2013.01); *B22D 25/02* (2013.01); *C22C 21/06* (2013.01)

(58) Field of Classification Search
CPC ..... A61C 17/34; A61C 17/22; A61C 17/3481; A46B 9/04
USPC .......................................................... 15/22.1
See application file for complete search history.

(56) References Cited

U.S. PATENT DOCUMENTS

2014/0023983 A1* 1/2014 Lowe ..................... A61C 7/006
433/24

* cited by examiner

*Primary Examiner* — Michael D Jennings

(57) ABSTRACT

The present invention relates to a toothbrush and provides an electric toothbrush comprising a hollow hand-held casing; the hand-held casing is disposed therein with a rechargeable lithium battery via a battery mount, and a brushless motor via a motor mount. The battery mount accommodates a PCT connected with the rechargeable lithium battery. The PCB is disposed with a control switch via a waterproof mount and a waterproof switch case. The press portion of the control switch is exposed from the switch hole of the hand-held casing. The vibration shaft of the brushless motor passes through the motor mount to an exterior of the hand-held casing. The vibration shaft is connected to a toothbrush head. The hand-held casing is threadedly connected to the rear cap at a bottom end thereof. The hand-held casing has a cross section in shape of a circle.

9 Claims, 2 Drawing Sheets

ELECTRIC TOOTHBRUSH

BACKGROUND OF THE INVENTION

The present invention relates to a toothbrush and more particularly pertains to an electric toothbrush and a hand-held casing thereof.

A toothbrush is a brush for cleaning teeth. In general, toothpaste is applied onto a toothbrush when brushing teeth to clean the teeth. Toothbrushes are daily necessities of people.

For the sake of convenience, people gradually use electric toothbrushes to brush their teeth. The electric toothbrushes available in the marketplace are inconvenient to charge and use and not safe enough to use. Furthermore, the internal arrangement of motors, batteries and so forth is not compact, thus occupying large space. They are heavy and inconvenient to carry.

Hand-held casings of electric toothbrushes are mostly made of plastic or alloy materials. Plastic materials are disadvantageous in that they are in general easy to deform, low in glossiness and mechanical strength, and easy to damage; besides, many plastic materials cannot fulfill environmental impact assessment standard. Alloy materials are high in mechanical strength, glossiness and smoothness, but they are prone by corrosion by acid or alkaline matters and is large in weight.

BRIEF SUMMARY OF THE INVENTION

In view of the aforesaid disadvantages now present in the prior art, the present invention provides an ultrasound toothbrush and a hand-held casing for electric toothbrush.

To attain this, the present invention comprises a toothbrush head, a motor mount, a hollow hand-held casing and a rear cap. The hand-held casing is disposed with a brushless motor and a battery mount therein. The battery mount accommodates a rechargeable lithium battery. The brushless motor is fixed in position by the motor mount mounted at a top end of the hand-held casing. The battery mount also accommodates a PCB connected with the rechargeable lithium battery. The PCB is disposed with a control switch via a waterproof mount and a waterproof switch case. The hand-held casing has a hole reserved for installation of the control switch. The brushless motor is disposed with a vibration shaft. The vibration shaft has a front end which passes through the motor mount to connect to the toothbrush head. The hand-held casing has a bottom end which threadedly connects to the rear cap.

The hand-held casing has a cross section in shape of a circle.

The brushless motor comprises the vibration shaft, a mount, a fixed front cap and a fixed rear cap. The mount is disposed with a pair of silicon steel sheets mounts arranged parallel to each other. The silicon steel sheets mounts (30) are disposed with silicon steel sheets thereon. The silicon steel sheets are encased by an enamel-insulated coil. The mount is disposed with a spring plate mount underneath. The spring plate mount is disposed with a stainless steel spring plate underneath. A left side and a right side of the spring plate mount are disposed with a second magnet and a first magnet respectively; a top side and a bottom side of the spring plate mount are disposed with a second press plate and a first press plate respectively. The first press plate and the second press plate fix the stainless steel spring plate, the spring plate mount, the first magnet and the second magnet into an integral body. The vibration shaft has a rear end which is provided with a slot corresponding to the stainless steel spring plate for connecting thereto. The stainless steel spring plate has a rear end which fixes on the fixed rear cap. The fixed front cap and the fixed rear cap are respectively disposed at a front end and a rear end of the mount to fix the aforementioned parts into an integral body.

The stainless steel spring plate has a rear end which is fixed on the fixed rear cap and a front end which inserts into the spring plate mount to connect to the vibration shaft. When the enamel-insulated coil generates magnetic field, the stainless steel spring plate is driven to oscillate leftward and rightward by the magnets, thereby driving the operation of the toothbrush head on the vibration shaft.

The fixed front cap is provided with a bearing for the vibration shaft to pass through. The bearing has a shaft hole whose diameter is larger than the vibration shaft, thereby restricting the oscillation amplitude of the vibration shaft and achieving a reasonable oscillation amplitude for teeth brushing.

The fixed front cap is fixed with the mount. The fixed front cap is disposed with a hollow hole for receiving the bearing. The front end of the vibration shaft passes through the bearing to connect to the toothbrush head, and the rear end thereof connects to the stainless steel spring plate.

The brushless motor is a brushless sonic vibration motor.

A vibration shaft waterproof casing is disposed between the vibration shaft and the motor mount. The vibration shaft waterproof casing is disposed on the vibration shaft.

A first waterproof O-ring is disposed between the motor mount and the hand-held casing. A second waterproof O-ring is disposed on a threaded connection portion between the rear cap and the hand-held casing.

The electric toothbrush is provided with a charging base. The charging base is provided with a DC plug. The rear cap is provided with a charging socket which is electrically connected with the rechargeable lithium battery. The DC plug is connected with a USB cable.

The present invention further relates to an improvement of a hand-held casing material, in particular:

A hand-held casing manufactured by the following method:

Step (1): Provide the following ingredients according to their parts by weight: 0.01 parts by weight of neodymium, 0.02 parts by weight of yttrium, 0.02 parts by weight of molybdenum, 0.03 parts by weight of niobium, 0.05 parts by weight of chromium, 0.05 parts by weight of zirconium, 0.06 parts by weight of zinc, 0.1 parts by weight of titanium, 0.2 parts by weight of magnesium, 1 part by weight of aluminum;

Step (2): Melt the aforementioned aluminum under protection of argon gas to 700° C. to obtain molten aluminum;

Step (3): Sequentially dispose the aforementioned neodymium, yttrium, molybdenum, niobium, chromium, zirconium, zinc, titanium and magnesium to a ball mill pot for mixing and ball-milling for 8 hours to obtain mixed metal powders;

Step (4): Switch on a resistance furnace and dispose the mixed metal powders obtained in Step (3) into a crucible and add N2 as protection gas; after the input materials are completely melted, add the molten aluminum obtained in Step (2) and continue to add N2 as protection gas; stir 5 minutes and finally add argon gas for refining for 15 minutes, and then mix evenly to obtain alloy solution;

Step (5): Inject the alloy solution obtained in Step (4) to a mold by a die-casting machine, with an injection pressure of 78 Mpa and an injection speed of 3.2 m/s to obtain the hand-held casing.

The beneficial effects of the present invention are mainly as follows:

The present invention is practical, low in manufacturing costs, convenient to use, quick to charge, comfortable to hold, brushes teeth electrically, saves effort, clean and sanitary, can be repeatedly use after recharge, thus prolonging product lifetime. The hand-held casing of the electrical toothbrush of the present invention is made of novel alloy material which has good mechanical properties, light in weight, low in costs, with a surface which does not decolor, smooth and glossy and without any corrosion. Molybdenum, niobium and zirconium increase the hardness and the plastic workability as well as the oxidation resistance and the corrosion resistance of the alloy material. Titanium has good heat and corrosion resistance and capable of maintaining good properties in various extreme conditions. The addition of neodymium to the alloy material can refine the microstructure of the alloy material, improve the mechanical properties of the alloy material, and increase plastic deformation of the alloy material, thus effectively refine structure, improve phase morphology and distribution, enhance bending resistance, hardness and other mechanical properties of the alloy material. The addition of magnesium reduces weight and increases glossiness.

Figure 1:
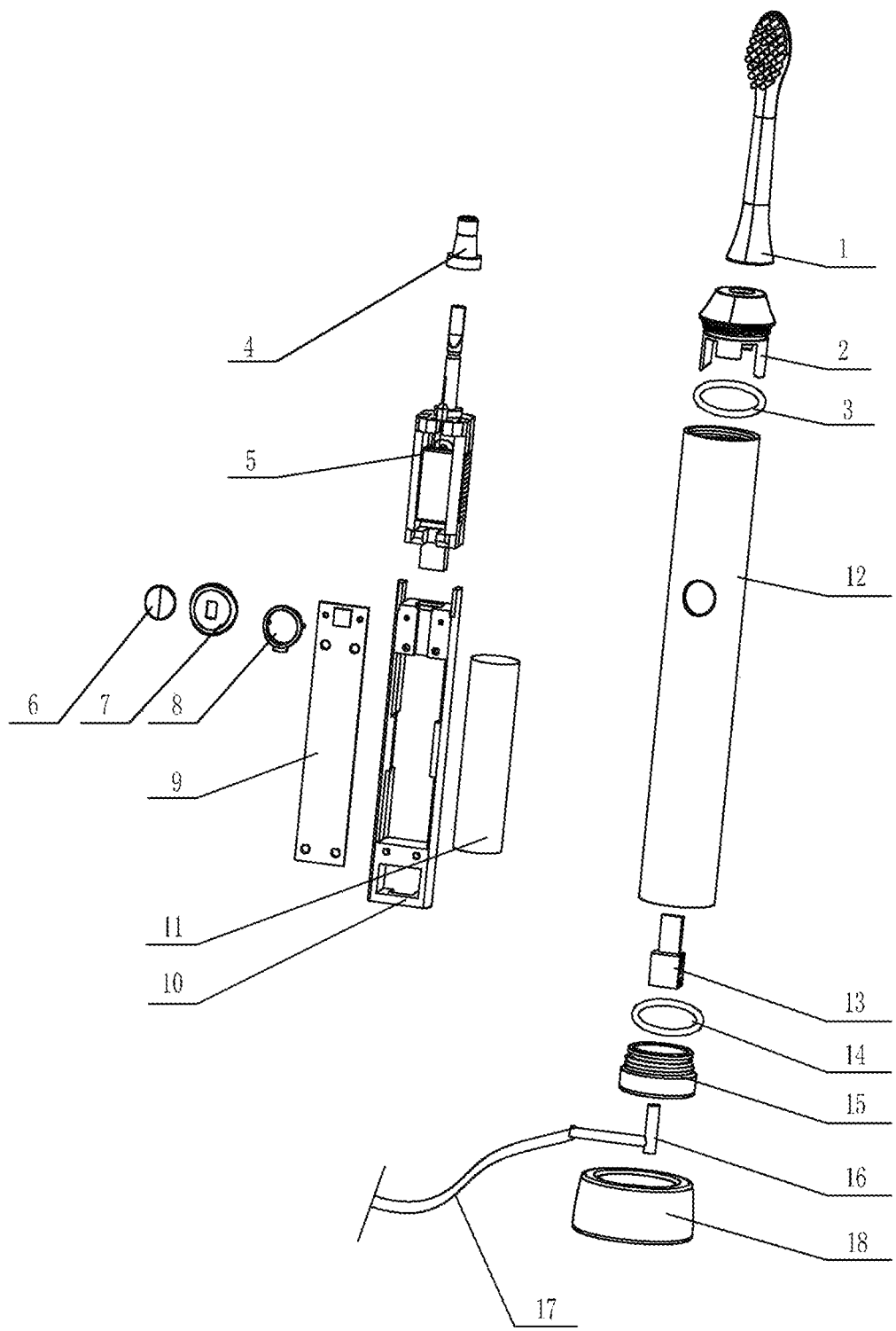
FIG. 1 is a disassembling view of the present invention.

In the drawings, 1 denotes toothbrush head; 2 denotes motor mount; 3 denotes first waterproof O-ring; 4 denotes waterproof casing; 5 denotes brushless motor; 6 denotes control switch; 7 denotes waterproof switch case; 8 denotes waterproof mount; 9 denotes PCB; 10 denotes battery mount; 11 denotes lithium battery; 12 denotes hand-held casing; 13 denotes waterproof socket; 14 denotes second waterproof O-ring; 15 denotes rear cap; 16 denotes DC plug; 17 denotes USB cable; 18 denotes charging base; 19 denotes fixed rear cap; 20 denotes stainless steel spring plate; 21 denotes first magnet; 22 denotes first spring plate; 23 denotes spring plate mount; 24 denotes second spring plate; 25 denotes second magnet; 26 denotes vibration shaft; 27 denotes silicon steel sheet; 28 denotes bearing; 29 denotes fixed front cap; 30 denotes silicon steel sheets mount; 31 denotes enamel-insulated coil; 32 denotes mount.

DETAILED DESCRIPTION OF THE INVENTION

In order to enable those skilled in the art to better understand the technical proposal of the present application, exemplary embodiments will be used to describe the present invention in a clearer and more complete manner. It is clear that the exemplary embodiments described are only a part of the embodiments of the present application, but not all embodiments. Based on the exemplary embodiments of the present application, all other embodiments obtained by those skilled in the art without any inventive efforts should fall within the scope of protection of the present application.

Embodiment 1

As illustrated in FIG. 1, the electric toothbrush comprises a toothbrush head 1, a motor mount 2, a hollow hand-held casing 12 and a rear cap 15. The hand-held casing 12 is disposed with a brushless motor 5 and a battery mount 10 therein. The battery mount 10 accommodates a rechargeable lithium battery 11. The brushless motor 5 is fixed in position by the motor mount 2 mounted at a top end of the hand-held casing 12. The battery mount 10 also accommodates a PCB 9 connected with the rechargeable lithium battery 11. The PCB 9 is disposed with a control switch 6 via a waterproof mount 8 and a waterproof switch case 7. The hand-held casing 12 has a hole reserved for installation of the control switch 6. The brushless motor 5 is disposed with a vibration shaft 26. The vibration shaft 26 has a front end which passes through the motor mount 2 to connect to the toothbrush head 1. The hand-held casing 12 has a bottom end which threadedly connects to the rear cap 15.

The operation of the brushless motor 5 is controlled by the control switch 6. The brushless motor 5 drives the vibration, extension and retraction of the toothbrush head 1 via the vibration shaft to achieve teeth brushing. At the same time, when the toothbrush head is slightly pressed, the vibration frequency and power of the toothbrush head increase.

The control switch 6 may be provided as a digital switch to control the brushless motor 5 to deliver four outputs, namely high-speed output, low-speed output, vibration output and soft output.

The hand-held casing 12 may be additionally disposed with a display screen to display the battery level of the rechargeable lithium battery 11, recharge reminder and operation mode.

The hand-held casing 12 has a cross section in shape of a circle.

Figure 2:
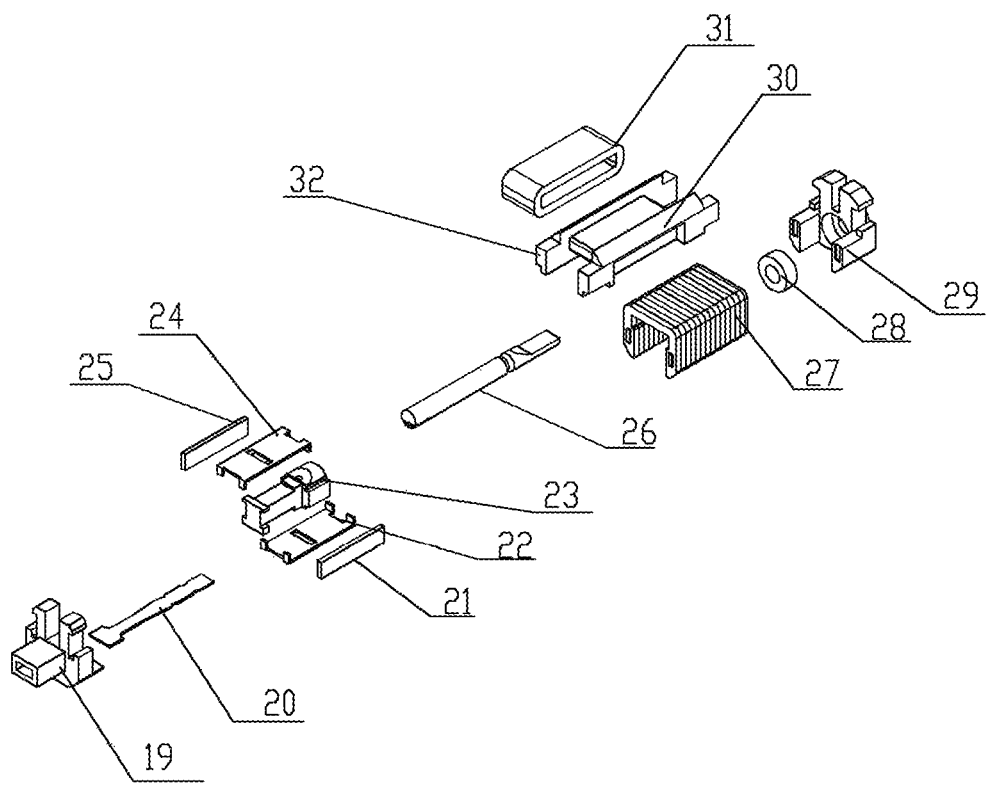
FIG. 2 is a disassembling view of the brushless motor of the present invention.

As illustrated in FIG. 2, the brushless motor 5 comprises a vibration shaft 26, a mount 32, a fixed front cap 29 and a fixed rear cap 19. The mount 32 is disposed with a pair of silicon steel sheets mounts 30 arranged parallel to each other. The silicon steel sheets mounts 30 are disposed with silicon steel sheets 27 thereon. The silicon steel sheets 27 are encased by an enamel-insulated coil 31. The mount 32 is disposed with a spring plate mount 23 underneath. The spring plate mount 23 is disposed with a stainless steel spring plate 20 underneath. A left side and a right side of the spring plate mount 23 are disposed with a second magnet 25 and a first magnet 21 respectively; a top side and a bottom side of the spring plate mount 23 are disposed with a second press plate 24 and a first press plate 22 respectively. The first press plate and the second press plate fix the stainless steel spring plate 20, the spring plate mount 23, the first magnet 21 and the second magnet 22 into an integral body. The vibration shaft 26 has a rear end which is provided with a slot corresponding to the stainless steel spring plate 20 for connecting thereto. The stainless steel spring plate 20 has a rear end which fixes on the fixed rear cap 19. The fixed front cap 29 and the fixed rear cap 19 are respectively disposed at a front end and a rear end of the mount 32 to fix the aforementioned parts into an integral body.

The fixed front cap is provided with a bearing for the vibration shaft to pass through. The bearing has a shaft hole whose diameter is larger than the vibration shaft, thereby restricting the oscillation amplitude of the vibration shaft and achieving a reasonable oscillation amplitude for teeth brushing.

The fixed front cap is fixed with the mount. The fixed front cap is disposed with a hollow hole for receiving the bearing 28. The front end of the vibration shaft 26 passes through the bearing to connect to the toothbrush head, and the rear end thereof connects to the stainless steel spring plate.

The brushless motor 5 is a brushless sonic vibration motor.

The stainless steel spring plate has a rear end which is fixed on the fixed rear cap and a front end which inserts into the spring plate mount to connect to the vibration shaft. When the enamel-insulated coil generates magnetic field, the stainless steel spring plate is driven to oscillate leftward and rightward by the magnets, thereby driving the operation of the toothbrush head on the vibration shaft.

A vibration shaft waterproof casing 4 is disposed between the vibration shaft 26 and the motor mount 2. The vibration shaft waterproof casing 4 is disposed on the vibration shaft.

A first waterproof O-ring 3 is disposed between the motor mount 2 and the hand-held casing. A second waterproof O-ring 14 is disposed on a threaded connection portion between the rear cap 15 and the hand-held casing.

The electric toothbrush is provided with a charging base 18. The charging base 18 is provided with a DC plug 16. The rear cap 15 is provided with a charging socket 13 which is electrically connected with the rechargeable lithium battery 11. The DC plug 16 is connected with a USB cable 17. To charge the electric toothbrush, position the electric toothbrush on the charging base 18 and the DC plug 16 is then inserted into the charging socket 13. The product could be charged repeatedly, thus prolonging product lifetime and reduces costs of use.

Embodiment 2

The hand-held casing for an electric toothbrush is manufactured according to the following method:

Step (1): Provide the following ingredients according to their parts by weight: 0.01 parts by weight of neodymium, 0.02 parts by weight of yttrium, 0.02 parts by weight of molybdenum, 0.03 parts by weight of niobium, 0.05 parts by weight of chromium, 0.05 parts by weight of zirconium, 0.06 parts by weight of zinc, 0.1 parts by weight of titanium, 0.2 parts by weight of magnesium, 1 parts by weight of aluminum. Step (2): Melt the aforementioned aluminum under the protection of argon gas to 700° C. to obtain molten aluminum. Step (3): Sequentially dispose the aforementioned neodymium, yttrium, molybdenum, niobium, chromium, zirconium, zinc, titanium and magnesium to a ball mill pot for mixing and ball-milling for 8 hours to obtain mixed metal powders. Step (4): Switch on a resistance furnace and dispose the mixed metal powders obtained in Step (3) into a crucible and add $N_2$ as protection gas; after the input materials are completely melted, add the molten aluminum obtained in Step (2) and continue to add $N_2$ as protection gas; stir 5 minutes and finally add argon gas for refining for 15 minutes, and then mix evenly to obtain alloy solution. Step (5): Inject the alloy solution obtained in Step (4) to a mold by a die-casting machine, with an injection pressure of 78 Mpa and an injection speed of 3.2 m/s to obtain the hand-held casing.

The hand-held casing has a material density of 2.67 g/cm$^2$, a tensile strength of 296 Mpa, a yield strength of 249 Mpa, an elongation of 9.3%, a hardness of 78 HB. Immerse the casing material to 5% sodium chloride solution for 240 hours; the resultant has a smooth and glossy surface with no corrosion spot, and there is no change to the mechanical properties.

Although the present application has been described by means of the exemplary embodiments above, but it is obvious to those skilled in the art that modifications and changes may be made on the basis of the present invention. Therefore, changes and modifications not deviated from the spirit of the present invention fall within the scope of the invention.

What is claimed is:

1. An electric toothbrush comprising a toothbrush head (1), a motor mount (2), a hollow hand-held casing (12) and a first rear cap (15); characterized in that the hand-held casing (12) is disposed with a brushless motor (5) and a battery mount (10) therein; the battery mount (10) accommodates a rechargeable lithium battery (11); the brushless motor (5) is fixed in position by the motor mount (2) mounted at a top end of the hand-held casing (12); the battery mount (10) also accommodates a PCB (9) connected with the rechargeable lithium battery (11); the PCB (9) is disposed with a control switch (6) via a waterproof mount (8) and a waterproof switch case (7); the hand-held casing (12) has a hole reserved for installation of the control switch (6); the brushless motor (5) is disposed with a vibration shaft (26); the vibration shaft (26) has a front end which passes through the motor mount (2) to connect to the toothbrush head (1); the hand-held casing (12) has a bottom end which threadedly connects to the first rear cap (15).

2. The electric toothbrush as in claim 1, characterized in that the hand-held casing (12) has a cross section in shape of a circle.

3. The electric toothbrush as in claim 1, characterized in that the brushless motor (5) comprises the vibration shaft (26), a mount (32), a fixed front cap (29) and a second fixed rear cap (19); the mount (32) is disposed with a pair of silicon steel sheets mounts (30) arranged parallel to each other, the silicon steel sheets mounts (30) are disposed with silicon steel sheets (27) thereon; the silicon steel sheets (27) are encased by an enamel-insulated coil (31); the mount (32) is disposed with a spring plate mount (23) underneath; the spring plate mount (23) is disposed with a stainless steel spring plate (20) underneath; a left side and a right side of the spring plate mount (23) are disposed with a second magnet (25) and a first magnet (21) respectively; a top side and a bottom side of the spring plate mount (23) are disposed with a second press plate (24) and a first press plate (22) respectively; the first press plate and the second press plate fix the stainless steel spring plate (20), the spring plate mount (23), the first magnet (21) and the second magnet (22) into an integral body; the vibration shaft (26) has a rear end which is provided with a slot corresponding to the stainless steel spring plate (20) for connecting thereto; the stainless steel spring plate (20) has a rear end which fixes on the second fixed rear cap (19); the fixed front cap (29) and the second fixed rear cap (19) are respectively disposed at a front end and a rear end of the mount (32) to fix the aforementioned parts into an integral body.

4. The electric toothbrush as in claim 3, characterized in that the fixed front cap (29) is provided with a bearing (28) for the vibration shaft (26) to pass through; the bearing has a shaft hole whose diameter is larger than the vibration shaft.

5. The electric toothbrush as in claim 3, characterized in that the brushless motor (5) is a brushless sonic vibration motor.

6. The electric toothbrush as in claim 1, characterized in that the brushless motor (5) is a brushless sonic vibration motor.

7. The electric toothbrush as in claim 1, characterized in that a vibration shaft waterproof casing (4) is disposed between the vibration shaft (26) and the motor mount (2); the vibration shaft waterproof casing (4) is disposed on the vibration shaft (26).

8. The electric toothbrush as in claim 7, characterized in that a first waterproof O-ring (3) is disposed between the motor mount (2) and the hand-held casing (12); a second waterproof O-ring (14) is disposed on a threaded connection portion between the first rear cap (15) and the hand-held casing (12).

9. The electric toothbrush as in claim 1, characterized in that the electric toothbrush is provided with a charging base (18); the charging base (18) is provided with a DC plug (16); the first rear cap (15) is provided with a charging socket (13) which is electrically connected with the rechargeable lithium battery (11); the DC plug (16) is connected with a USB cable (17).

\* \* \* \* \*